(12) United States Patent
Young

(10) Patent No.: US 9,345,855 B2
(45) Date of Patent: May 24, 2016

(54) CATHETER GRIP AND CATHETER ASSEMBLY

(71) Applicant: Tim Young, Moorabbin (AU)

(72) Inventor: Tim Young, Moorabbin (AU)

(73) Assignee: Sayco Pty. Ltd., Moorabbin Victoria (AU)

( * ) Notice: Subject to any disclaimer, the term of this patent is extended or adjusted under 35 U.S.C. 154(b) by 124 days.

(21) Appl. No.: 14/012,741

(22) Filed: Aug. 28, 2013

(65) Prior Publication Data

US 2014/0066905 A1 Mar. 6, 2014

(30) Foreign Application Priority Data

Aug. 29, 2012 (AU) .................................. 2012903716

(51) Int. Cl.
*A61M 25/00* (2006.01)
*A61M 25/01* (2006.01)
*A61M 25/09* (2006.01)
*A61F 2/95* (2013.01)

(52) U.S. Cl.
CPC ......... *A61M 25/002* (2013.01); *A61M 25/0017* (2013.01); *A61M 25/01* (2013.01); *A61M 25/013* (2013.01); *A61M 25/0111* (2013.01); *A61M 25/0113* (2013.01); *A61F 2002/9517* (2013.01); *A61M 25/09041* (2013.01); *A61M 2210/1085* (2013.01); *A61M 2210/1089* (2013.01); *A61M 2210/1096* (2013.01)

(58) Field of Classification Search
CPC .................... A61M 25/0113; A61M 25/0111; A61M 25/013; A61M 25/002; A61M 2210/1096; A61M 25/01; A61M 2210/1089; A61M 2210/1085; A61M 2210/1092; A61M 5/3275; A61F 2002/9517
See application file for complete search history.

(56) References Cited

U.S. PATENT DOCUMENTS

| | | | | |
|---|---|---|---|---|
| 4,553,961 A | | 11/1985 | Pohndorf et al. | |
| 4,627,838 A | * | 12/1986 | Cross et al. | 604/105 |
| 4,713,057 A | * | 12/1987 | Huttner et al. | 604/164.07 |
| 4,867,172 A | * | 9/1989 | Haber | A61B 5/1438 600/576 |
| 5,073,166 A | * | 12/1991 | Parks et al. | 604/175 |
| 5,242,398 A | * | 9/1993 | Knoll et al. | 604/103.05 |
| 5,401,257 A | * | 3/1995 | Chevalier, Jr. et al. | 604/265 |
| 5,423,784 A | | 6/1995 | Metz | |
| 5,454,798 A | * | 10/1995 | Kubalak et al. | 604/328 |
| 5,643,280 A | * | 7/1997 | Del Rio et al. | 606/109 |
| 2001/0053892 A1 | * | 12/2001 | Parmigiani | 604/197 |
| 2002/0103460 A1 | * | 8/2002 | Kubalak et al. | 604/171 |
| 2003/0018322 A1 | * | 1/2003 | Tanghoj | A61F 5/44 604/544 |
| 2003/0181872 A1 | * | 9/2003 | Newby | 604/263 |
| 2003/0229297 A1 | * | 12/2003 | Christensen et al. | 600/585 |
| 2006/0041269 A1 | | 2/2006 | Horrigan | |
| 2008/0082120 A1 | | 4/2008 | Mauch et al. | |

(Continued)

FOREIGN PATENT DOCUMENTS

| | | |
|---|---|---|
| EP | 0 667 126 B1 | 3/1999 |
| WO | WO 03/080168 A1 | 10/2003 |
| WO | WO 2006/085331 A2 | 8/2006 |

*Primary Examiner* — Adam Marcetich
(74) *Attorney, Agent, or Firm* — Reinhart Boerner Van Deuren P.C.

(57) ABSTRACT

A catheter grip and catheter assembly are provided. The catheter grip includes a body portion adapted to extend circumferentially around a catheter shaft of the catheter assembly to facilitate gripping of the catheter shaft by a user. The catheter grip also includes a head portion through which the catheter shaft can be fed and a biasing mechanism. The biasing mechanism biases the body portion and the head portion away from one another.

19 Claims, 9 Drawing Sheets

(56) References Cited

U.S. PATENT DOCUMENTS

| | | |
|---|---|---|
| 2009/0043287 A1 | 2/2009 | Mosler et al. |
| 2010/0286664 A1* | 11/2010 | Haslinger ............... 604/533 |
| 2010/0312227 A1 | 12/2010 | House |
| 2011/0276013 A1* | 11/2011 | Saitoh et al. ............ 604/263 |

* cited by examiner

SECTION J-J

SECTION M-M

CATHETER GRIP AND CATHETER ASSEMBLY

CROSS-REFERENCE TO RELATED PATENT APPLICATIONS

This patent application claims priority to Australian Application No. 2012903716, filed Aug. 29, 2012, the entire teachings and disclosure of which are incorporated herein by reference thereto.

FIELD OF INVENTION

The present invention relates to a catheter grip and catheter assembly. In particular, the invention relates to a catheter grip in the form of a resiliently biased grip that assists with insertion of the catheter, and catheters provided with such a catheter grip.

BACKGROUND OF THE INVENTION

Urinary catheters are known and generally include a latex, polyurethane, or silicone tube that is inserted into a patient's bladder via the urethra. Catheterisation allows the patient's urine to drain freely from the bladder for collection. Urinary catheters may also be used to inject liquids used for treatment or diagnosis of bladder conditions. A clinician or nurse usually performs the catheterisation procedure, but self-catheterisation is also possible. If long term catheterisation is needed, catheters that facilitate self-catheterisation are most desirable to give patients a greater degree of independence.

Urinary catheters may be permanent (indwelling catheters), or may be intermittent and removed after each catheterisation. A Foley catheter (indwelling urinary catheter) is retained by means of a balloon at the tip of the catheter that is inflated with sterile water. The balloons typically come in two different sizes: 5-10 ml and 30 ml and are commonly made in silicone rubber or natural rubber. An intermittent catheter, or Robinson catheter, is a flexible catheter used for short term drainage of urine. Unlike the Foley catheter, it has no balloon on its tip and therefore cannot stay in place unaided. These can be non-coated or coated, for example they may be coated with a hydrophilic coating, and are generally packaged ready for use. Coudé catheters are designed with a curved tip that makes it easier to pass the catheter through the curvature of the prostatic urethra. Hematuria (or haematuria) catheters are a type of Foley catheter used for Post-TURP hemostasis. This is useful following endoscopic surgical procedures, or in the case of gross hematuria. There are both two-way and three-way hematuria catheters (i.e. double and triple lumen). External, Texas, urisheath, and condom catheters are generally used for incontinent males and carry a lower risk of infection than an indwelling catheter.

For some patients the insertion and removal of a catheter causes discomfort or pain, so a topical anesthetic is sometimes used. As mentioned above, in many cases catheterisation is performed as a sterile medical procedure by trained, qualified personnel, using equipment designed for this purpose. In the case of intermittent self-catheterisation, patients are trained to perform the procedure themselves. Intermittent self-catheterisation is performed by the patient four to six times a day, using a clean technique in most cases. Incorrect technique may cause trauma to the urethra or prostate (male), urinary tract infection, or a paraphimosis in the uncircumcised male. For patients with spinal cord lesions and neurogenic bladder dysfunction, intermittent catheterisation (IC) is a standard method for bladder emptying. The technique is safe and effective and results in improved kidney and upper urinary tract status, lessening of vesicoureteral reflux and amelioration of continence. In addition to the clinical benefits, patient quality of life is enhanced by the increased independence and security offered by self-catheterisation.

In order to maximise the potential for sterile insertion of catheters and thereby minimise the chances of urinary tract infection during self-catheterisation, a number of designs for catheter packaging have been proposed. The designs generally aim to remove the need for direct physical contact with the catheter during insertion. For example, in some instances the catheter is packaged within a bag from which it is fed by a user via indirect contact through the bag. In this example, the bag may contain a lubricant to assist with feeding of the catheter. In other examples, the catheter is removable from a package and is provided with a sleeve through which the catheter may be fed. In this example, a user pinches the sleeve to indirectly engage the catheter and facilitate insertion.

The options that are currently available can be cumbersome and difficult to use if a user is self-inserting the catheter shaft. Furthermore, in many instances users of catheters have reduced or limited hand and/or arm function. In such cases, catheters provided with packaging and sleeves as discussed above can be even more difficult to insert.

The subject matter claimed herein is not limited to embodiments that solve any disadvantages or that operate only in environments such as those described above. Rather, this background is only provided to illustrate one exemplary technology area where some embodiments described herein may be practice.

SUMMARY OF THE INVENTION

In one aspect the invention provides a catheter grip for a catheter shaft, the catheter grip comprising:
  a body portion adapted to extend circumferentially around the catheter shaft to facilitate gripping of the catheter shaft by a user;
  a head portion through which the catheter shaft can be fed; and
  a biasing mechanism,
wherein the biasing mechanism biases the body portion and the head portion away from one another.

As used herein the term "mechanism" includes one or more parts that act to achieve a desired result, in this case biasing of the body portion and head portion of the catheter grip away from one another. The term is not intended to be limited to examples that require two or more interacting parts.

The arrangement of biasing mechanism is not particularly limited, provided the body portion and head portion are biased away from one another. As will be discussed below, this biasing mechanism makes feeding of a catheter shaft passing through the catheter grip easier, particularly for patients who have limited or diminished hand or arm function. In particular, single handed operation may be achieved. In one embodiment, the biasing mechanism is disposed between the body portion and the head portion.

Likewise, the form of biasing mechanism is not particularly limited, provided it achieves the requisite function. For example, the biasing mechanism may include a spring mechanism. In one embodiment, the biasing mechanism comprises at least two laterally spaced walls extending between the body portion and the head portion, the laterally spaced walls being resiliently deformable to provide the biasing. Each of the laterally spaced walls may comprise a weakened or diminished portion at or around a longitudinal mid-point thereof such that, in use, as the body portion is forced towards the head portion the laterally spaced walls flex outwardly to provide the biasing.

In one embodiment, the body portion comprises two opposed gripping surfaces that are resiliently compressible towards one another to facilitate gripping of the catheter shaft by a user. Direct contact with the catheter shaft is thereby avoided and the risk of infection reduced. The body portion may comprise opposed longitudinal walls that extend between edges of the opposed gripping surfaces. In a particularly preferred embodiment, opposed gripping surfaces are provided and the biasing mechanism comprises at least two laterally spaced walls extending between the body portion and the head portion in the same plane as the opposing gripping surfaces, the laterally spaced walls being resiliently deformable to provide the biasing, as discussed above.

In one embodiment, the head portion comprises a collar. Where the biasing mechanism comprises at least two laterally spaced walls extending between the body portion and the head portion, the laterally spaced walls are connected directly to, or are integral with the collar. In certain embodiments, the head portion includes a shaft feed extending from the collar through which the catheter shaft is fed. In certain embodiments, the shaft feed is disposed on a feed insert that is adapted to be inserted into the collar of the head portion, or which is disposed on the collar (i.e. surrounding the collar). The feed insert may comprise a tubular portion having at least one ridge, the tubular portion being received by the collar of the head portion, an abutment having an abutment surface which abuts the collar of the head portion, and the shaft feed which extends from an outer face of the abutment.

In certain embodiments, the body portion, head portion and biasing mechanism are integral with one another to provide the catheter grip. For example the catheter grip may comprise an injection moulded integral unit. Of course, the catheter grip may be produced by any suitable method and is not so limited.

Another aspect of the present invention relates to a catheter assembly comprising:
  a catheter shaft having a drainage outlet at a proximal end thereof and a catheter tip and at least one drainage inlet at a distal end thereof; and
  a catheter grip associated with the catheter shaft, the catheter grip comprising a body portion that extends circumferentially around the catheter shaft and facilitates gripping of the catheter shaft by a user, and a head portion through which the catheter shaft can be fed,
  wherein the catheter grip comprises a biasing mechanism that biases the body portion and the head portion away from one another.

As discussed above, the biasing mechanism may be disposed between the body portion and the head portion. For example, the biasing mechanism may comprise at least two laterally spaced walls extending between the body portion and the head portion, the laterally spaced walls being resiliently deformable to provide the biasing. Again, in certain embodiments each of the laterally space walls comprises a weakened or diminished portion at or around a longitudinal mid-point thereof such that, in use, as the body portion is forced towards the head portion the laterally spaced walls flex outwardly to provide the biasing.

Again, the body portion may comprise two opposed gripping surfaces that are resiliently compressible towards one another to facilitate gripping of the catheter shaft by a user. The body portion may comprise opposed longitudinal walls that extend between edges of the opposed gripping surfaces. In preferred embodiments, the gripping surfaces are provided and the biasing mechanism includes opposed and laterally spaced walls that extend between the body portion and the head portion, and which are in the same plane as the gripping surfaces.

In certain embodiments, the head portion comprises a collar as discussed above. The head portion may also comprise a shaft feed extending from the collar through which the catheter shaft is fed. The shaft feed may be disposed on a feed insert that is adapted to be inserted into or onto the collar of the head portion. The feed insert may comprise a tubular portion having at least one ridge, the tubular portion being received by the collar of the head portion, an abutment having an abutment surface which abuts the collar of the head portion, and the shaft feed which extends from an outer face of the abutment.

The body portion, head portion and biasing mechanism may be integral with one another to provide the catheter grip.

The drainage outlet may comprise a catheter funnel, or other form of outlet employed in the art. Likewise, the at least one drainage inlet of the catheter shaft may be any that are currently available in the art, for example the at least one drainage inlet may comprise at least one eyelet.

The present invention consists of features and a combination of parts hereinafter fully described and illustrated in the accompanying drawings, it being understood that various changes in the details may be made without departing from the scope of the invention or sacrificing any of the advantages of the present invention.

BRIEF DESCRIPTION OF ACCOMPANYING DRAWINGS

To further clarify various aspects of some embodiments of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the accompanying drawings in which.

DETAILED DESCRIPTION OF THE PREFERRED EMBODIMENTS

Figure 1:
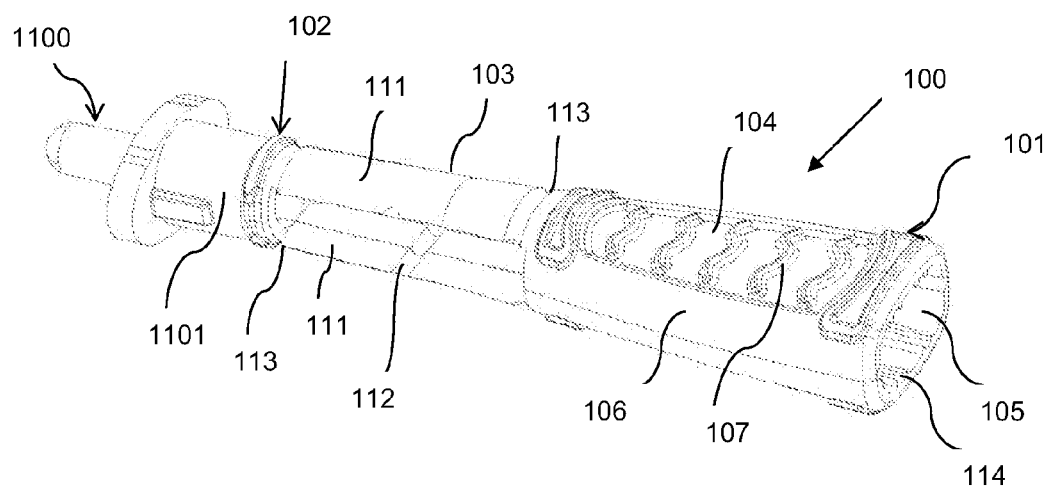
FIG. 1 illustrates a perspective view of the catheter grip of an embodiment of the invention, including a tip insert.
Figure 2:
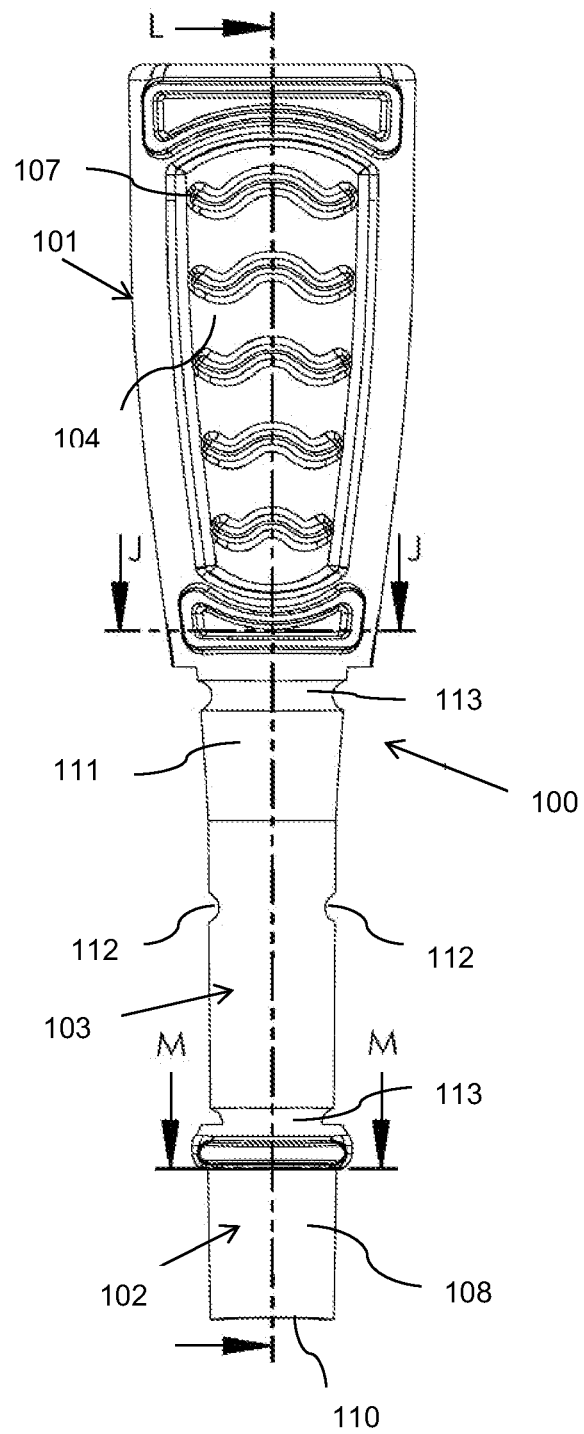
FIG. 2 illustrates a plan view of the catheter grip of FIG. 1, excluding the tip insert.
Figure 3:
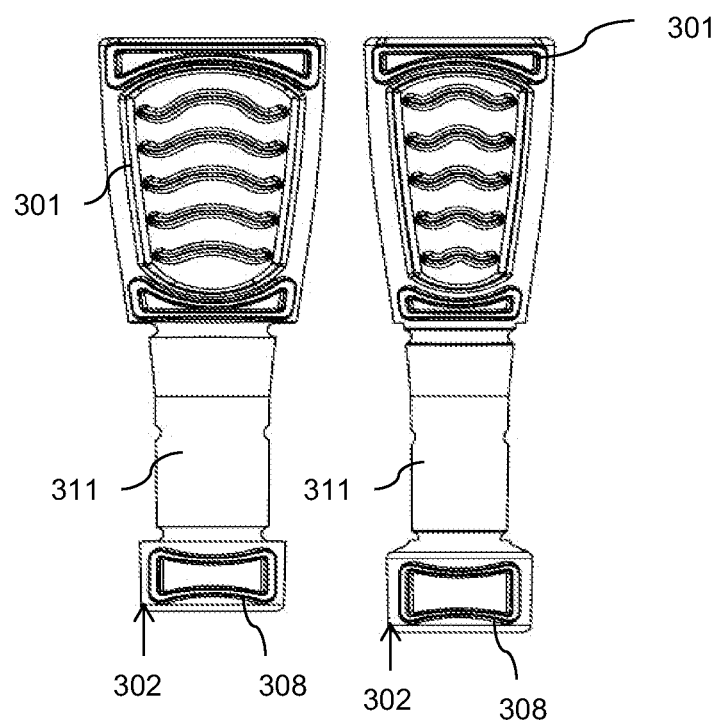
FIGS. 3A and 3B illustrate plan views of alternative embodiments of the catheter grip of the invention.
Figure 4:
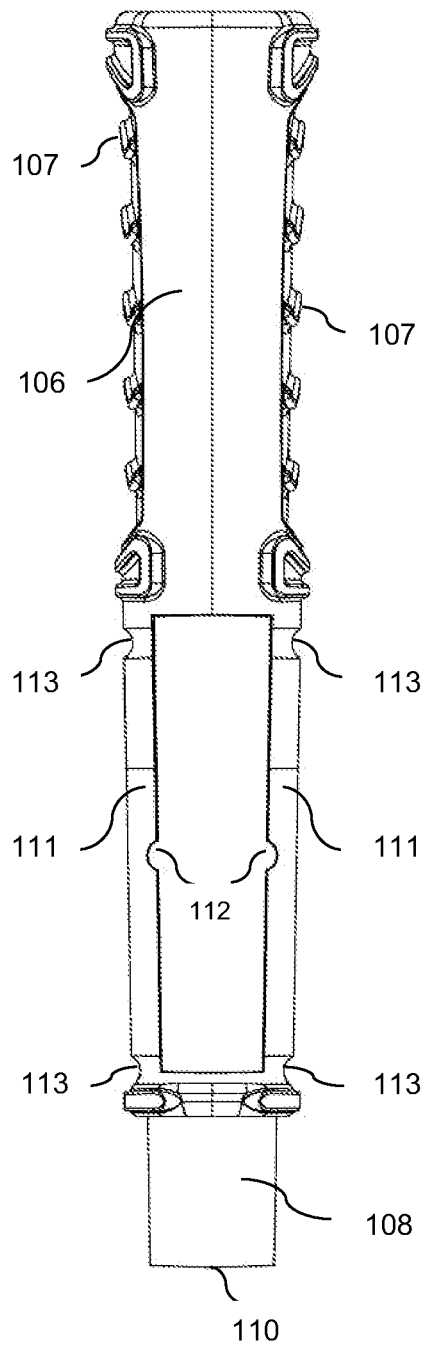
FIG. 4 illustrates a side view of the catheter grip of FIG. 1.
Figure 5:
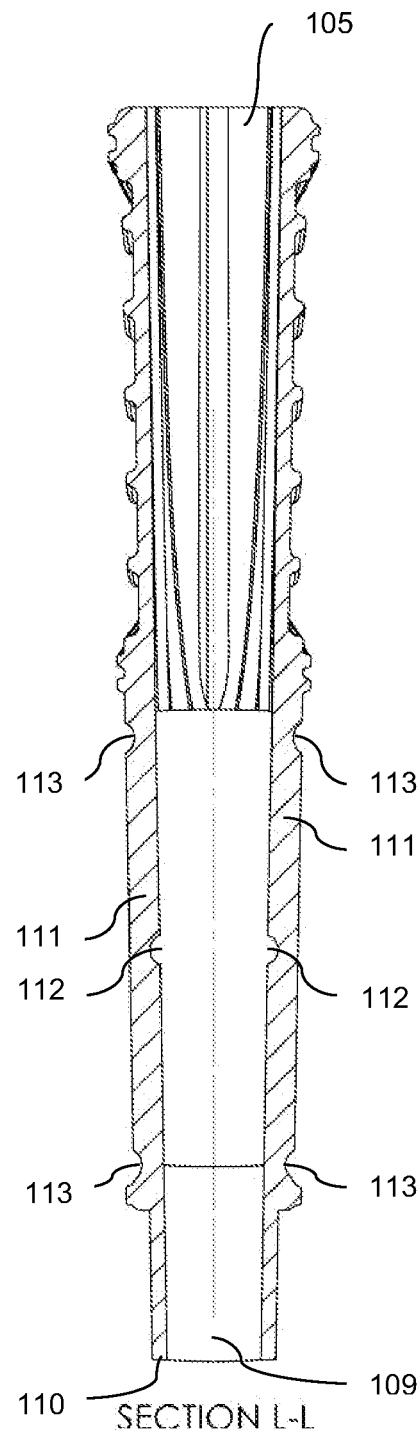
FIG. 5 illustrates a sectional view (Section L-L) of the catheter grip of FIG. 1.
Figure 6:
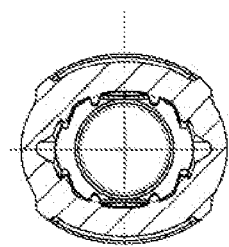
FIG. 6 illustrates a sectional view (Section J-J) of the catheter grip of FIG. 1.
Figure 7:
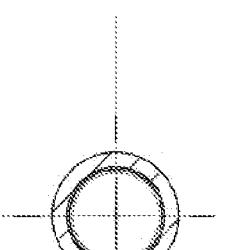
FIG. 7 illustrates a sectional view (Section M-M) of the catheter grip of FIG. 1.
Figure 8:
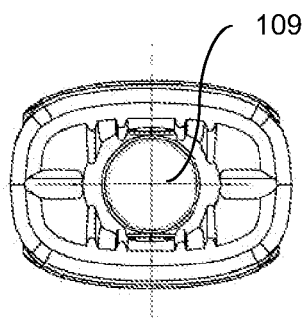
FIG. 8 illustrates an end view of the catheter grip of FIG. 1.

The present invention provides a catheter assembly and catheter grip. In particular, the invention relates to catheters provided with a resiliently biased grip that assists with insertion of the catheter.

Hereinafter, this specification will describe the present invention according to the preferred embodiments. It is to be understood that limiting the description to the preferred embodiments of the invention is merely to facilitate discussion of the present invention and it is envisioned without departing from the scope of the appended claims.

Referring to FIGS. 1 to 8, a catheter grip 100 is provided. The catheter grip 100 includes a body portion 101 and a head portion 102 that joined through an interposed biasing mechanism 103. As such, the body portion 101, head portion 102 and biasing mechanism 103 are an integral unit.

The body portion 101 is of a generally frustoconical shape and includes opposed gripping surfaces 104. The gripping surfaces 104 are compressible towards one another such that a catheter shaft (not shown) that extends through the passage 105 defined by the body member 101 can be indirectly gripped by a user of the catheter grip 100. Generally, the material forming the gripping surfaces 104 will be thinner than the material forming the remainder of the body portion 101, thereby giving the gripping surfaces 104 more flexibility than the remainder of the body portion.

The body portion 101 includes opposed longitudinal walls 106 that extend between edges of the opposed gripping surfaces 104. The material forming the longitudinal walls 106 is, as discussed above, thicker than that forming the gripping surfaces 104 to provide the longitudinal walls 106 with greater rigidity and structural strength. The gripping surfaces 104 are also provided with ridges 107 to assist with gripping of the catheter shaft through the gripping surfaces 104.

As illustrated in FIGS. 3A and 3B, the dimensions of the body portion 301 may vary without dramatically affecting the operation of the catheter grip 300. Likewise, the form and dimensions of the collar 308 forming the head portion 302 may vary, as may those of the lateral walls 311. A more preferred form of the catheter grip 100 may be gleaned from FIG. 2, which includes a relatively narrow body portion 101, collar 108 and lateral walls 111 (i.e. compared with those of the catheter grips 300 of FIGS. 3A and 3B).

The head portion 102 includes a collar 108 that defines an aperture 109 through which the catheter shaft extends. An insert 1100 may be fitted onto the collar 108 or inserted into the aperture 109. As discussed in more detail below, the insert 1100 includes a tubular portion 1101 that is complementary with the aperture 109 and which receives or is inserted into the collar 108. An abutment located on the insert includes an abutment surface that abuts an outer edge 110 of the collar 108. A catheter feed is also provided on the insert which extend from the abutment, away from the collar 108 of the head portion 102. The catheter feed is complementary with the catheter shaft and is generally formed from a thin polymeric material that lightly engages the catheter shaft as it passes there through. In particular, the shaft feed lightly engages the catheter to ensure that the catheter shaft passes through catheter feed without difficulty, but so that the catheter shaft cannot easily retract back through the catheter feed.

The biasing mechanism 103 includes two opposed longitudinal walls 111. The longitudinal walls 111 are formed from a resilient material, as is the remainder of the catheter grip 100. Each longitudinal wall 111 includes a weakened or diminished portion 112, in this case grooves that traverse inner surfaces of the longitudinal walls 111 at or around a longitudinal mid-point thereof. Weakened or diminished portions 113 may also be provided at either end of the longitudinal walls 111.

The lateral walls 111 are disposed in the same plane as the gripping surfaces 104. It has been found that such an arrangement advantageously ensures appropriate outward flexing of the lateral walls 111 in use, as discussed below. However, as discussed hereafter, other arrangements are considered within the ambit of the present invention.

A number of longitudinally extending alignment ribs 114 on inner surfaces of the gripping surfaces 104. The alignment ribs 114 advantageously maintain the position of the catheter shaft when it is gripped by a user during insertion. That is, lateral movement of the catheter shaft within the catheter grip 100 is minimised.

Figure 9:
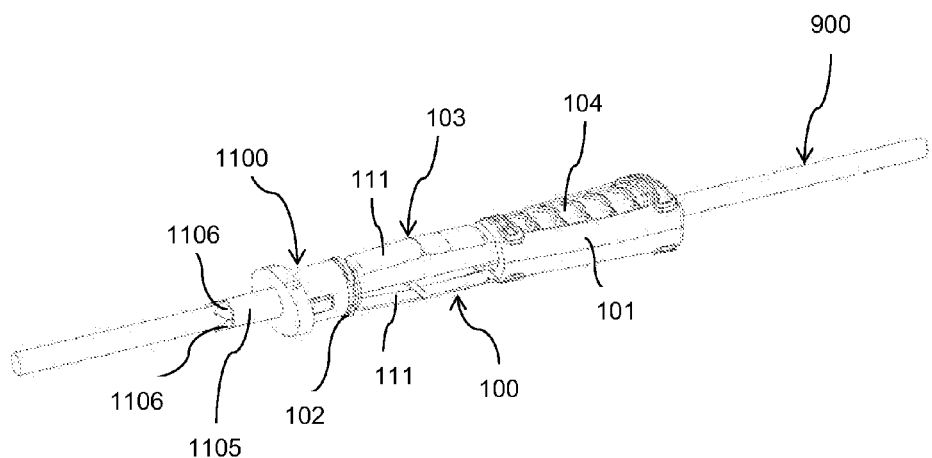
FIG. 9 illustrates the catheter grip of FIG. 1 on a catheter shaft.
Figure 10:
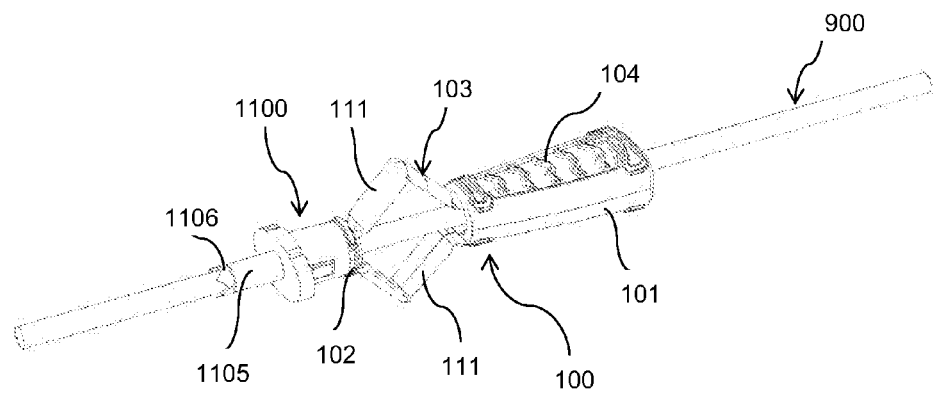
FIG. 10 illustrates the catheter grip of FIG. 1 on a catheter shaft in a flexed position.

In use, as illustrated in FIGS. 9 and 10, a user of the catheter grip 100 grips a catheter shaft 900 passing through the catheter grip 100 by compressing the two gripping surfaces 104 towards one another with finger and thumb. Once the catheter shaft 900 is gripped, the user forces the body portion 101 towards the head portion 102 against the bias of the biasing mechanism 103. The catheter shaft thereby passes through the head portion 102 and tip insert 1100 and is inserted into the user or patient. In doing so, the longitudinal walls 111 of the biasing mechanism 103 flex outwardly until the body portion 101 approaches or abuts the head portion 102. The user of the catheter grip 100 can then release their grip of the gripping surfaces 104, thereby releasing their grip on the catheter shaft 900. The biasing mechanism 103, on release of the user's grip on the catheter shaft 900, biases the body portion 101 away from the head portion 102, while the position of the catheter shaft 900 relative to the head portion 102 is maintained due to light engagement of the tip insert 1100 with the catheter shaft 900, as discussed with reference to FIG. 1100. As such, effectively a length of the catheter shaft 900 corresponding to the length of the longitudinal walls 111 has been fed through the head portion 102 and into the user or patient. This process may be repeated until a desired length of the catheter shaft 900 has been inserted into the user or patient.

Figure 11:
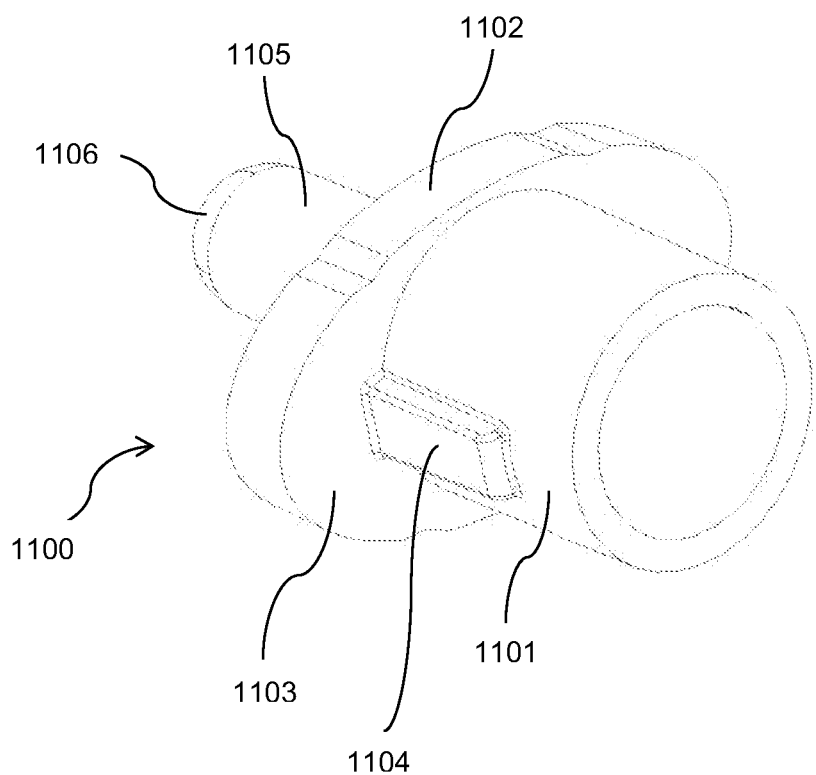
FIG. 11 illustrates a tip insert.

A tip insert 1100 for the catheter grip 100 is illustrated in FIG. 11. The tip insert 1100 includes a tubular portion 1101 that is generally inserted into the aperture 109 of the collar 108 of the head portion 102. The tip insert 1100 includes an abutment 1102 that provides an abutment surface 1103. On insertion of the tip insert 1100 into the collar 108, the outer edge 110 of the collar 108 abuts the abutment surface 1103. Ridges 1104 are provided to ensure frictional engagement of the tip insert 1100 in the collar 108. A feed portion 1105 fittingly receives the catheter shaft 900 and includes flexible tabs 1106 that flare outwardly as the catheter shaft 900 passed through the feed portion 1105. The flexible tabs 1106 facilitate light engagement of the catheter shaft 900 by the feed portion 1105 of the tip insert 1100 preventing retraction of the catheter shaft 900 back into the catheter grip 100 during feeding of the catheter shaft 900 through the feed portion 1105.

Figure 12:
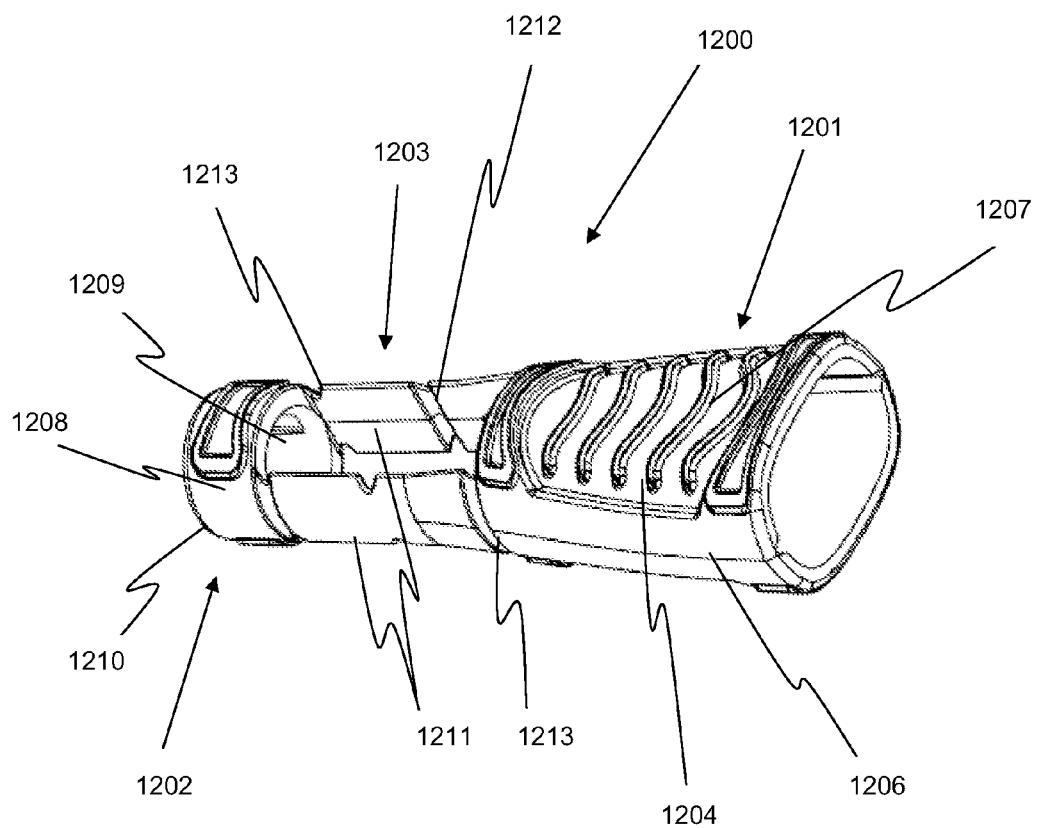
FIG. 12 illustrates a perspective view of the catheter grip of an alternative embodiment of the invention.

Referring to FIG. 12, an alternative embodiment of a catheter grip 1200 is illustrated. The catheter grip 1200 again includes a body portion 1201 and a head portion 1202 that joined through an interposed biasing mechanism 1203. The body portion 1201 is again of a generally frustoconical shape and includes opposed gripping surfaces 1204. The gripping surfaces 1204 are compressible towards one another such that a catheter shaft (not shown) can be indirectly gripped by a user of the catheter grip 1200.

The body portion 1201 again includes opposed longitudinal walls 1206 that extend between edges of the opposed gripping surfaces 1204. Ridges 1207 are provided to assist with gripping of the catheter shaft through the gripping surfaces 1204.

The head portion 1202 includes a collar 1208 that defines an aperture 1209 through which the catheter shaft extends. An insert can also be provided, as discussed previously.

The biasing mechanism 1203 includes two opposed longitudinal walls 1211 including a weakened or diminished portion 1212 at or around a longitudinal mid-point thereof and weakened or diminished portions 1213 at either end of the longitudinal walls 1211. In this embodiment, the lateral walls 1211 are disposed in a plane that is transverse to that of the gripping surfaces 1204.

The catheter shaft may be lubricated if desired and the form of packaging is also not particularly limited. Generally, it is envisaged that the catheter assembly will be packaged in an elongate package with a tear off or tear open tab facilitating easy access to the catheter assembly with minimal effort.

Unless the context requires otherwise or specifically stated to the contrary, integers, steps or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of steps, elements or integers. Thus, in the context of this specification, the term "comprising" is used in an inclusive sense and thus should be understood as meaning "including principally, but not necessarily solely".

It will be appreciated that the foregoing description has been given by way of illustrative example of the invention and that all such modifications and variations thereto as would be apparent to persons of skill in the art are deemed to fall within the broad scope and ambit of the invention as herein set forth.

The invention claimed is:

1. A catheter grip for a catheter shaft, said catheter grip comprising:
   a body portion adapted to extend circumferentially around said catheter shaft, said body portion comprising two opposed substantially planar gripping surfaces that are resiliently compressible towards one another to facilitate gripping of said catheter shaft by a user, and opposed longitudinal walls that extend between edges of said opposed substantially planar gripping surfaces;
   a head portion through which said catheter shaft can be fed;
   a biasing mechanism comprising two laterally spaced walls extending between said body portion and said head portion, said laterally spaced walls being resiliently deformable away from one another as said body portion and said head portion are moved towards one another such that, on release, said laterally spaced walls bias said body portion and said head portion away from one another; and
   wherein said catheter grip is adapted to be removably associated with said catheter shaft.

2. A catheter grip according to claim 1, wherein each of said laterally spaced walls comprises a weakened or diminished portion at or around a longitudinal mid-point thereof such that, in use, as said body portion is forced towards said head portion said laterally spaced walls flex outwardly to provide said biasing.

3. A catheter grip according to claim 2, wherein each of said laterally spaced walls comprises a weakened or diminished portion adjacent the head portion and/or the body portion.

4. A catheter grip according to claim 1, wherein said opposed gripping surfaces are disposed in the same plane as said opposed laterally spaced walls.

5. A catheter grip according to claim 1, wherein said head portion comprises a collar.

6. A catheter grip according to claim 5, wherein said head portion additionally comprises a shaft feed extending from said collar through which said catheter shaft is fed.

7. A catheter grip according to claim 6, wherein said shaft feed is disposed on a feed insert that is adapted to be inserted into said collar of said head portion.

8. A catheter grip according to claim 7, wherein said feed insert comprises a tubular portion having at least one ridge, said tubular portion being received by said collar of said head portion, an abutment having an abutment surface which abuts said collar of said head portion, and said shaft feed which extends from an outer face of said abutment.

9. A catheter grip according to claim 1, wherein said body portion, head portion and biasing mechanism are integral with one another to provide said catheter grip.

10. A catheter grip according to claim 1, wherein inner surfaces of one or more of said opposed, substantially planar gripping surfaces of said body portion comprise longitudinally extending alignment ribs.

11. A catheter grip according to claim 1, wherein said opposed, substantially planar gripping surfaces of said body portion comprise ridges extending laterally there across.

12. A catheter assembly comprising:
    a catheter shaft having a drainage outlet at a proximal end thereof and a catheter tip and at least one drainage inlet at a distal end thereof;
    a catheter grip removably associated with said catheter shaft, said catheter grip comprising a body portion that extends circumferentially around said catheter shaft, said body portion comprising two opposed substantially planar gripping surfaces that are resiliently compressible towards one another to facilitate gripping of said catheter shaft by a user, and opposed longitudinal walls that extend between edges of said opposed substantially planar gripping surfaces, and a head portion through which said catheter shaft can be fed;
    a biasing mechanism comprising two laterally spaced walls extending between said body portion and said head portion, said laterally spaced walls being resiliently deformable away from one another as said body portion and said head portion are moved towards one another such that, on release, said laterally spaced walls bias said body portion and said head portion away from one another.

13. A catheter assembly according to claim 12, wherein each of said laterally spaced walls comprises a weakened or diminished portion at or around a longitudinal mid-point thereof such that, in use, as said body portion is forced towards said head portion said laterally spaced walls flex outwardly to provide said biasing.

14. A catheter assembly according to claim 13, wherein each of said laterally spaced walls comprises a weakened or diminished portion adjacent the head portion and/or the body portion.

15. A catheter assembly according to claim 12, wherein said drainage outlet comprises a catheter funnel.

16. A catheter assembly according to claim 12, wherein said at least one drainage inlet of said catheter shaft comprises at least one eyelet.

17. A catheter assembly according to claim 12, wherein inner surfaces of one or more of said opposed, substantially planar gripping surfaces of said body portion comprise longitudinally extending alignment ribs.

18. A catheter assembly according to claim 12, wherein said opposed, substantially planar gripping surfaces of said body portion comprise ridges extending laterally there across.

19. A catheter assembly according to claim 12, wherein said opposed, substantially planar gripping surfaces are disposed in the same plane as said opposed laterally spaced walls.

\* \* \* \* \*